United States Patent [19]
Bell et al.

[11] Patent Number: 5,481,057
[45] Date of Patent: Jan. 2, 1996

[54] ALKYLATION WITH ACTIVATED EQUILIBRIUM FCC CATALYST

[75] Inventors: Weldon K. Bell, Pennington; Tracy J. Huang, Lawrenceville, both of N.J.; Rudolph M. Lago, Yardley; Ying-Yen P. Tsao, Lahaska, both of Pa.; D. Duayne Whitehurst, Titusville, N.J.

[73] Assignee: Mobil Oil Corporation, Fairfax, Va.

[21] Appl. No.: 217,819

[22] Filed: Mar. 25, 1994

[51] Int. Cl.$^6$ .................. C07C 2/58; C07C 4/06
[52] U.S. Cl. .......... 585/722; 585/314; 585/324; 585/330; 585/331; 585/653; 585/709
[58] Field of Search .................. 585/312, 313, 585/324, 330, 331, 709, 722, 648, 653

[56] References Cited

U.S. PATENT DOCUMENTS

| | | | |
|---|---|---|---|
| 3,251,902 | 5/1966 | Garwood et al. | 585/722 |
| 4,454,241 | 6/1984 | Pine et al. | 502/68 |

*Primary Examiner*—Ponnathapura Achutamurthy
*Attorney, Agent, or Firm*—Alexander J. McKillop; Malcolm D. Keen; Richard D. Stone

[57] ABSTRACT

A process for catalytic cracking and C3/C4 olefin alkylation with phosphorus stabilized faujasite catalyst is disclosed. Catalytic cracking produces C3 and C4 olefins, which are alkylated using phosphorus stabilized and water activated cracking catalyst. Spent alkylation catalyst may be discharged into the FCC unit.

10 Claims, 1 Drawing Sheet

ALKYLATION WITH ACTIVATED EQUILIBRIUM FCC CATALYST

FIELD OF THE INVENTION

This invention relates to fluid catalytic cracking and alkylation of light olefins.

DESCRIPTION OF RELATED ART

The process of the present invention makes unconventional use of equilibrium catalyst (E-Cat) from an FCC unit to overcome problems in production of alkylate. Both FCC and conventional olefins alkylation are briefly reviewed, followed by an in depth review of problems in production of alkylate.

Fluidized catalytic cracking (FCC) of hydrocarbons has enjoyed worldwide success. It is the method of choice for converting a heavy feed into lighter, more valuable products, the most valuable of which are usually the high octane gasoline and the light olefins. Catalytic cracking occurs in the absence of externally added H2 in contrast to hydrocracking in which H2 is added. An inventory of catalyst cycles between a cracking reactor and a catalyst regenerator. In FCC feed contacts 60–80 micron catalyst in a reactor at 425° C.–600° C., usually 460° C.–560° C. The hydrocarbons crack, and deposit coke on the catalyst. Cracked products are separated from the coked catalyst, which is stripped of volatiles, usually with steam, and then regenerated. In the catalyst regenerator, coke is burned, restoring catalyst activity and heating the catalyst to 500° C.–900° C., usually 600° C.–750° C.

Most older FCC units regenerate the spent catalyst in a single dense phase fluidized bed of catalyst. Although there are myriad individual variations, typical designs are shown in U.S. Pat. No. 3,849,291 (Owen) and U.S. Pat. No. 3,894,934 (Owen et al), and U.S. Pat. No. 4,368,114 (Chester et at.) which are incorporated by reference. Many newer units use high efficiency designs, with a fast fluidized bed coke combustor, dilute phase transport riser, and second dense bed to collect regenerated catalyst.

A further description of the catalytic cracking process may be found in the monograph, "Fluid Catalytic Cracking With Zeolite Catalysts", Venuto and Habib, Marcel Dekker, New York, 1978, incorporated by reference. A discussion of FCC products, and downstream upgrading processes follows.

FCC vapor products are typically fractionated into light, olefin rich gas, gasoline, light and heavy cycle oils, and slurry oils. The olefinic light gasses are usually purified and separated, with the C3 and C4 olefins usually converted to gasoline boiling range material. The cycle oils are sold as fuel, or recycled to the FCC reactor.

FCC thus produces a spectrum of products, from dry gas to slurry oil. Some of the cleanest transportation fuels are made from the light olefins, via sulfuric or HF alkylation. This alkylate is essentially free of aromatics and contains almost no sulfur. Some of the dirtiest fuels are made in FCC, with FCC gasoline containing significant amounts of sulfur and aromatics. The FCC heavy naphtha is especially troublesome, having large amounts of sulfur. Refiners have heretofore blended clean and dirty fuels in their gasoline pool and met product specifications, but this has become increasingly difficult due to legislative changes. Refiners would like to make more use of alkylation, but this is not always possible.

Alkylation of light olefins with isobutane to make alkylate is a mature technology. Both HF and sulfuric alkylation are practiced extensively commercially. In these processes light olefins from the FCC unit, and from such other olefin generators as may be present in or near the refinery, are mixed with large amounts of isobutane or other alkylating agent. Olefins, isobutane and liquid acid mix, the acid promotes alkylation reactions which form high octane alkylate. This alkylate has a high octane number, and is clean, low in sulfur because it is made from such clean starting materials.

Both HF and sulfuric acid alkylation require large inventories of toxic acid. In the case of HF, there is concern that an acid cloud may form if there were a plant upset. Many refiners would like to develop an alternative to existing liquid acid alkylation techniques to convert FCC light olefins into more valuable, clean liquid transportation fuels.

Some other olefin conversion technologies are known. Solid phosphoric acid (SPA) can oligomerize light olefins into an olefinic gasoline of fair to poor quality.

Zeolite based catalyst alkylation processes have been proposed, using an acidic crystalline material such as zeolite X or Y as the acid acting catalyst.

Garwood et al, in U.S. Pat. No. 3,251,902, taught use of rare earth exchanged zeolite X for alkylation of isobutane with ethylene and propylene. This patent is incorporated by reference.

While the '902 approach completely avoids the use of large amounts of liquid acid there are problems relating to catalyst activity and stability, materials handling, and product recovery.

Catalyst activity and stability are a problem because zeolite catalysts rapidly deactivate during the alkylation reaction. Catalyst activity can be restored to some extent by oxidative regeneration, but this is expensive and not completely satisfactory. Refiners with FCC units typically have large amounts, hundreds of tons, of equilibrium catalyst available, but this E-Cat does not have enough activity to be an effective isoparaffin alkylation catalyst. Fresh or makeup FCC catalyst does have sufficient activity, but the amounts of makeup catalyst required for the FCC may not mesh with the amount of catalyst required for alkylation.

Materials handling is a problem because of the diffusion limited reactions which take place. For catalyst to be used efficiently, it must be of such a small size that it is hard to handle. If oil dropped spheres or extrudates of REY roughly $\frac{1}{16}$th inch were used, the catalyst would be easy to handle but relatively ineffective due to diffusion limitations. Only about 3% of the intrinsic activity would be available for use in alkylation. Even catalyst of approximately FCC sized particles, 50 microns, uses only about 65% of its intrinsic activity. Thus macropore diffusion limitations are severe, so small sized catalyst particles are essential. This dictates the use of less than 100 micron catalyst particles, which greatly complicates catalyst recovery and reuse and products recovery, which are reviewed next.

Products recovery can be difficult in a commercial unit because filtration of less than 100 micron particles from alkylate is difficult. Cyclones, filters, etc all work, but leave some solids in the liquid. These solids represent a loss of catalyst and a product contaminant that must be removed. Fractionation will usually be necessary for product recovery, and any fractionators used must be designed to accommodate the presence of substantial amounts of solids, i.e., slant trays, drains on low spots, pump flushing lines, etc. Such measures have been taken for decades in FCC units. Fines tolerant fractionators and pumps can be readily cost-justified for use In large FCC units but are much harder to justify for smaller units, such as paraffin alkylation units which are 1/5th or 1/10 the size of the FCC unit, in terms of weight of products.

Some idea of the size and complexity of the problem can be gleaned from Journal articles such as CENTRIFUGATION/FILTRATION Successfully Cope With FCC Catalyst Fines, Tore H. Lindstrom and Reza Hashemi, Chemical Engineering Progress (August 1993), which is incorporated by reference. Use of fine particles, such as those from an FCC unit, overcomes diffusion limitations, but creates many problems.

We wanted to provide refiners with a way to upgrade light olefins generated by FCC units which did not require a large inventory of hazardous liquids, such as HF or $H_2SO_4$. We wanted to be able to upgrade olefins, using catalyst with a small size, so that diffusion limitations would not be too great, but also wanted to avoid the cost of a fines tolerant alkylate fractionator. We wanted to be able to tap into the tremendous reservoir of E-cat available in cracking refineries, and increase the activity of this material sufficiently to permit its use as an alkylation catalyst. We also wanted to be able to regenerate the alkylation catalyst, without purchasing a separate alkylation catalyst regenerator.

We were able to achieve the seemingly incompatible goals by using a special FCC catalyst (or modifying E-Cat), and closely integrating the alkylation unit with the FCC unit. By using a phosphorus stabilized or modified large pore zeolite cracking catalyst, and an unexpectedly effective water activation treatment, we could increase the activity of E-cat sufficiently so that it could be used as an effective alkylation catalyst.

Phosphorus treatment of zeolites, and the effect of water on such phosphorus treated materials will be briefly reviewed.

Phosphorus stabilized shape selective zeolites are well known and widely used. U.S. Pat. No. 3,962,364, Young teaches alkylation in the presence of phosphorus-modified ZSM-5. U.S. Pat. No. 3,965,208, Butter et al, teaches methylation of toluene using ZSM-5 modified by the addition of phosphorus, arsenic or antimony. U.S. Pat. No. 3,972,832 Butter and Kaeding claims a shape selective zeolite with at least 0.78 wt % phosphorus in the crystal structure, while a Division, U.S. Pat. No. 4,044,065 claims conversion using this phosphorus containing zeolite. U.S. Pat. No. 4,356,338 Young discloses extending catalyst life by treating a shape selective zeolite with phosphorus and/or steam. These patents on phosphorus treatment/stabilization of shape selective zeolites, such as ZSM-5, are incorporated by reference.

Phosphorus stabilized large pore cracking catalyst is also known. Pine et al, U.S. Pat. No. 4,454,241, incorporated by reference, disclosed clay derived Y zeolite activated with dihydrogen phosphate or dihydrogen phosphite anion had increased cracking activity.

Although phosphorus treatment of zeolites is widely known, the fragility of the phosphorus/zeolite bond has also been reported. Molecules of phosphoric acid which have interacted with the strong acid sites on the zeolite "can easily be removed by extraction . . . " Ohlymann et el, CATALYSIS ON ZSM-5 ZEOLITES MODIFIED BY PHOSPHORUS, Catalysis and Adsorption by Zeolites, Elsevier 1991, Page 13.

All known commercial processes using phosphorus stabilized zeolite are believed to operate either water free, or at high temperatures. FCC catalyst is steamed during the stripping step, but steaming occurs at temperatures of 900° to 1000° F. (near the riser top temperature) so no liquid water ever sees catalyst. The FCC regenerator typically contains 5–10 psi steam partial pressure (from water of combustion and entrained stripping steam), but operates at 1200° –1400° F.

We were able to devise a water based activation treatment which increased the activity of phosphorus containing catalyst.

Using an unusual FCC catalyst, and an unlikely activation procedure, we could improve the activity of E-Cat sufficiently to achieve effective paraffin alkylation without undue diffusion limitations. By closely integrating the alkylation process with the FCC process we overcame, or avoided, most of the material handling and product recovery problems associated with fine particle catalysts.

BRIEF SUMMARY OF THE INVENTION

Accordingly, the present invention provides a process for alkylating at least one of propylene and butylene with an activated, faujasite based alkylation catalyst comprising incorporating from 0.5 to 5 wt % phosphorus, on a finished catalyst basis, into a catalyst comprising faujasite in an amorphous matrix to produce a phosphorus containing catalyst having a cracking catalyst activity as determined by the alpha test; activating said phosphorus containing catalyst by contact with steam or water in an amount sufficient to increase the alpha activity at least 100%; alkylating at least one of said butene and propylene with isobutane at olefin alkylation conditions to produce alkylate.

In another embodiment, the present invention provides a combined fluidized catalyst cracking (FCC) and olefin alkylation process for conversion of 650° F.+ hydrocarbons to products including catalytically cracked naphtha and alkylate comprising contacting said feed with a stream of regenerated, phosphorus containing equilibrium cracking catalyst (E-Cat) having an average particle size within the range of 60–80 microns and an alpha activity in a cracking reactor to produce cracked products including naphtha boiling range material and light olefins including propylene and butylene and spent catalyst; separating cracked products from spent catalyst in a product fractionator and gas purification plant to produce a naphtha boiling range product and a light olefin product stream comprising at least one of propylene and butylene; stripping spent catalyst with steam to produce stripped catalyst; regenerating said stripped catalyst in a catalyst regeneration means by contact with an oxygen containing gas to produce regenerated, phosphorus containing E-Cat and flue gas containing entrained catalyst and fines; recycling to said cracking reactor a major portion greater than 50% of said regenerated E-Cat; charging to an activation reactor a minor portion less than 50% of said regenerated E-Cat and activating said E-Cat by contact with water or steam at catalyst activation conditions sufficient to increase the alpha activity of the E-Cat at least 100% and produce activated E-Cat; charging said activated E-Cat to an alkylation reactor for use as alkylation catalyst; alkylating at olefin alkylation conditions in said alkylation reactor isobutane and at least a portion of said light olefinic product comprising at least one of propylene and butylene to produce alkylate and spent alkylation catalyst; recovering by settling, flashing, or fractionation alkylate from spent alkylation catalyst to produce alkylate as a product of said alkylation process and to produce spent alkylation catalyst; recycling, at least periodically, said spent alkylation catalyst to said regenerator.

Other preferred embodiments relate to activation of the catalyst by contact with liquid water to form an aqueous slurry of alkylation catalyst and water, use of a continuous stirred tank reactor (CSTR) wherein said light olefin product is added, and recovery of unreacted isobutane by continuously withdrawing product from said CSTR and flashing to recover isobutane.

BRIEF DESCRIPTION OF THE DRAWINGS

The FIGURE is a process flow diagram of a preferred embodiment, an alkylation unit integrated with an FCC unit.

DETAILED DESCRIPTION

Figure 1:
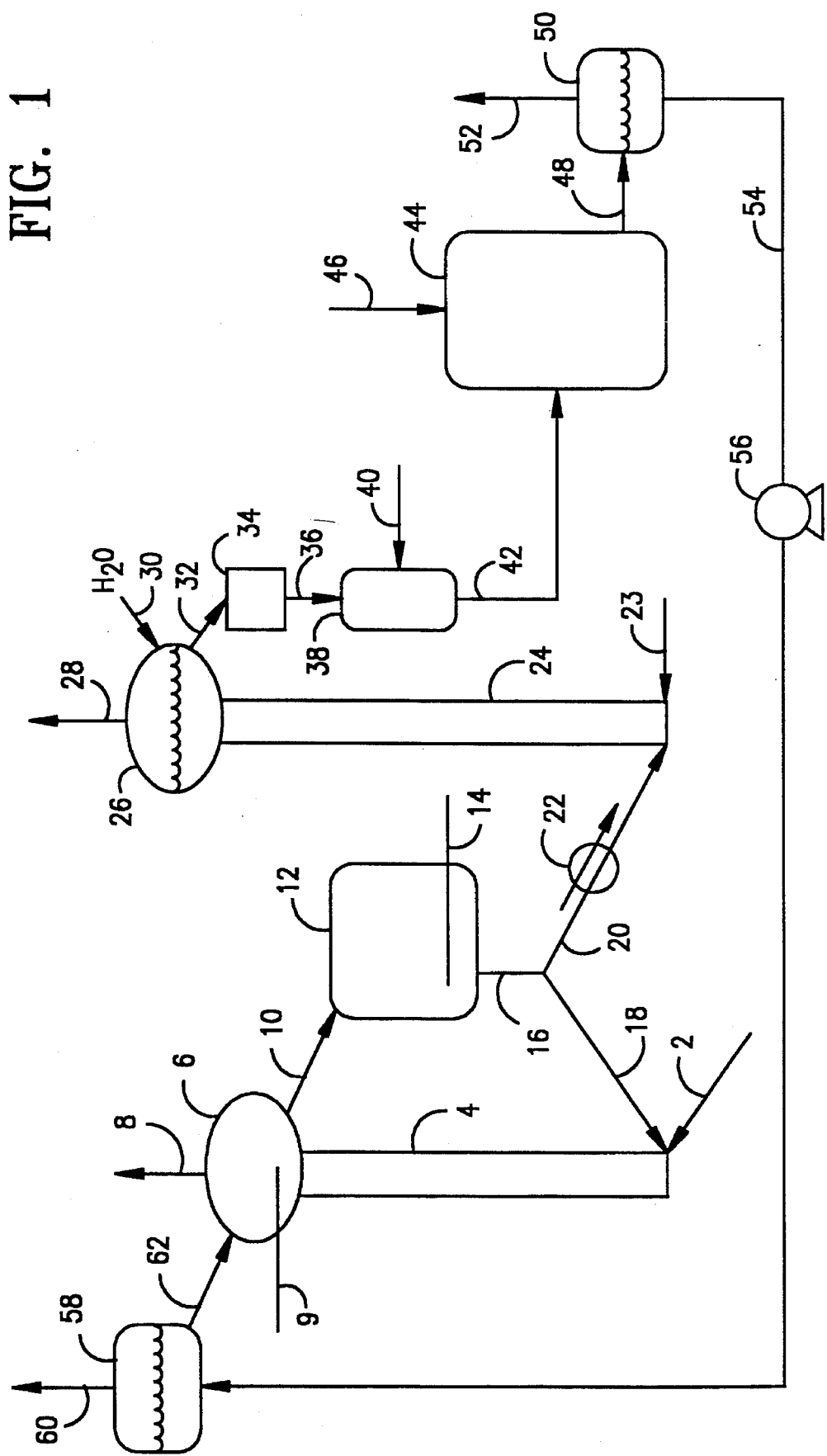

The invention can be better understood with reference to the FIGURE. Most of the items discussed can be conventional, i.e., a conventional FCC unit, and FCC main fractionator. The drawing review starts with the FCC unit, and then addresses the alkylation units. The FIGURE is a gross oversimplification of a complex, but mature, process FCC. More details on FCC may be taken from U.S. Pat. No. 5,082,983, which is incorporated by reference.

A heavy feed, typically a gas oil boiling range material, is charged via line 2 to mix with a light alkylate stream in line 135, and the mixture is charged to the lower end of a riser cracking FCC reactor 4. Hot regenerated catalyst is added via conduit 15 to the riser. Preferably some atomizing steam is added, by means not shown, to the base of the riser, usually with the feed. The heavy hydrocarbon feed and catalyst mixture rises as a generally dilute phase through riser 4. A cracked mixture is discharged into separator 6, which usually includes one or more stages of cyclone separation not shown. Steam is added via line 9 to aid in stripping cracked products from spent catalyst discharged from the riser. Cracked products are removed line 8 and sent to the FCC main column, not shown, for product recovery.

The riser 4 top temperature usually ranges from about 480° to 615° C. (900° and 1150° F.), and preferably between about 538° and 595° (1000 and 1050° F.). The riser top temperature is usually controlled by adjusting the catalyst to oil ratio in riser 4 or by varying feed preheat.

Cracked products are fractionated in the main column, not shown, to recover various liquid product fractions including gasoline and normally gaseous materials, including olefin rich C3 and C4 hydrocarbons which are purified and recovered in an unsaturated gas plant, not shown.

An olefin rich stream, preferably light olefins generated in the cat cracker and recovered from the FCC main column or purchased olefins from an outside source, are added to the alkylation reactor 44 via line 46. Catalyst for the alkylation reaction is equilibrium catalyst, or E-Cat, removed from the FCC regenerator 12 via lines 16 and 20. This catalyst, which is removed at the regenerator temperature of 1200° to 1500° F., is preferably cooled by indirect heat exchange means 22 and charged to the base of lift means 24. Water, steam, or i-C4 may be added via line 23 for use as a lift medium, to transport cooled E-Cat to separator/hydrator 26. Catalyst and lift gas are separated by conventional means, such as a cyclone separator, or simple settling separation. Water or steam is added via line 30 to hydrate and activate the E-Cat. If the catalyst is over-hydrated, as will be the case when a liquid water phase forms on the catalyst, it is preferably dried by means not shown prior to use. A suitable phosphorus compound is preferably incorporated into the cracking catalyst from the time of its manufacture, but phosphorus may be added via the lift stream 23, or the water stream 30, or some other means not shown.

The activated catalyst is withdrawn via line 32 and charged through isolation hopper 34. Activated catalyst is removed via line 36 from the hopper and enters mixing tank 38 to contact iso-butane added via line 40. The resulting mixture is charged via line 42 to alkylation reactor 44. C3 and/or C4 olefins are added via line 46 to alkylation reactor 44 via line 46. This reactor is preferably a stirred tank reactor, or may contain packing or trays designed to promote contact of hydrocarbon liquids with catalyst. Alkylated paraffins, unreacted olefins, and (at least intermittently) some catalyst are removed via line 48 and charged via line 48 to flash vessel 50. Unconverted isobutane, and any unconverted light olefins, propane and inerts are removed as a vapor phase via line 52 and charged to isobutane recovery, not shown, or burned as fuel.

Alkylate is removed via line 54 and slurry pump 56 to alkylate flash 58, which may be a single stage V/L separator as shown, or a fractionation means. Alkylate is removed via line 60, and may be added to the refinery gasoline pool, sent to a dedicated fractionator, or added to the FCC main column. Separator 58 need only free the alkylate from the slurry catalyst phase, which is charged via line 62 to the FCC unit. Preferably this slurry containing spent alkylation catalyst is added to or above the FCC catalyst stripper, the coolest place in the FCC reactor/regenerator where the alkylate product may be recovered without cracking it. The slurry may also be added to the liquid FCC feed in line 2, charged into the riser reactor via a slurry injection nozzle not shown, or charged to the FCC regenerator.

Having provided an overview of the process, more details will now be provided about each step.

FCC FEED

Any conventional FCC feed can be used. The feeds may range from the typical, such as petroleum distillates or residual stocks, either virgin or partially refined, to the atypical, such as coal oils and shale oils. Preferred feeds are gas oils, vacuum gas oils, atmospheric resids, and vacuum resids. The feeds usually will have an initial boiling point above about 650° F.

FCC CATALYST

Any commercially available, or hereafter developed, faujasite based FCC catalyst may be used. The catalyst should contain some, usually at least 5 wt % faujasite, in a porous refractory matrix such as silica-alumina, clay, or the like. The zeolite is usually 5–40 wt % of the catalyst, with the rest being matrix.

Zeolite X may be used, and will provide satisfactory activity and stability both for FCC use and as an alkylation catalyst when it has been properly stabilized with phosphorus.

Faujasite, or aluminum deficient forms of faujasite such as dealuminized Y (DEAL Y), ultrastable Y (USY) and ultrahydrophobic Y (UHP Y) zeolites may be used.

The faujasites may be stabilized with Rare Earths, e.g., 0.1 to 30 wt % RE.

The catalyst inventory may contain one or more additives, present as separate additive particles, or mixed in with each particle of the cracking catalyst. Additives can be added to enhance octane (medium pore size zeolites, sometimes referred to as shape selective zeolites, i.e., those having a Constraint Index of 1–12, and typified by ZSM-5, and other materials having a similar crystal structure).

Phosphorus stabilization of the neat faujasite is preferred. Ideally the large pore zeolite is stabilized with phosphorus prior to mixing with clay or other amorphous support. Phosphorus may also be added to either virgin FCC catalyst, or to E-Cat withdrawn from the FCC unit, and this phosphorus modified material charged to the alkylation unit.

FCC REACTOR CONDITIONS

Conventional cracking conditions may be used. Typical riser cracking reaction conditions include catalyst/oil ratios of 0.5:1 to 15:1 and preferably 3:1 to 8:1. The catalyst-oil contact time will usually be 0.1–50 seconds, and preferably 0.5 to 5 seconds, and most preferably about 0.75 to 4 seconds, with riser top temperatures of 900° to about 1050° F.

It is important to have good mixing of feed with catalyst in the base of the riser reactor, using conventional techniques such as adding large amounts of atomizing steam, multiple nozzles, use of atomizing nozzles and similar technology.

It is preferred, but not essential, to have the riser reactor discharge into a closed cyclone system for rapid and efficient separation of cracked products from spent catalyst. A preferred closed cyclone system is disclosed in U.S. Pat. No. 4,502,947 to Haddad et al, which is incorporated by reference.

It is preferred but not essential, to rapidly strip the catalyst just as it exits the riser, and upstream of the conventional catalyst stripper. Stripper cyclones disclosed in U.S. Pat. No. 4,173,527, Schatz and Heffley, which is incorporated by reference, may be used.

It is preferred, but not essential, to use a hot catalyst stripper. Hot strippers heat spent catalyst by adding some hot, regenerated catalyst to spent catalyst. Suitable hot stripper designs are shown in U.S. Pat. No. 3,821,103, Owen et al, which is incorporated herein by reference. If hot stripping is used, a catalyst cooler may be used to cool the heated catalyst before it is sent to the catalyst regenerator. A preferred hot stripper and catalyst cooler is shown in U.S. Pat. No. 4,820,404, Owen, which is incorporated by reference.

The FCC reactor and stripper conditions, per se, can be conventional.

FCC CATALYST REGENERATION

The process and apparatus of the present invention can use conventional FCC regenerators. Many of these operate at 1200° to 1600° F. A high efficiency regenerator may be used. The essential elements of a high efficiency regenerator include a coke combustor, a dilute phase transport riser and a second dense bed. These regenerators are widely known and used. The process can also use single dense bed regenerators, or other designs, such as multi-stage regenerators, etc.

The regenerator, per se, forms no part of the present invention. More details about catalyst regeneration may be taken from the many FCC patents incorporated by reference.

ALKYLATION CATALYST

The alkylation catalyst may be E-Cat containing phosphorus which has been activated by hydration. Several catalyst components must be present—faujasite, phosphorus and water. Conventional E-Cat will contain large amounts of faujasite, typically 10–40% Y zeolite, based on the zeolite content of the makeup catalyst. It is well known that the cracking catalyst loses crystallinity in the high temperature steam laden environment of FCC units, and that equilibrium catalyst contains less crystal than the makeup catalyst, but it is the convention among refiners to refer the zeolite content of the makeup catalyst rather than the zeolite content of the E-Cat.

Preferably the E-Cat comes from a phosphorus stabilized X or Y zeolite makeup cracking catalyst. Alternatively the makeup catalyst may be phosphorus free, and the E-Cat charged to the hydrator can be impregnated or exchanged to contain sufficient phosphorus upstream of the hydrator.

The catalyst should contain sufficient phosphorus to stabilize the Y zeolite, and respond to hydration activation. Generally this will require at least 0.1 moles of phosphorus per mole of zeolitic framework aluminum. Preferably the catalyst contains 0.2 to 2 moles of phosphorus per mole of framework aluminum, and most preferably 0.3 to 0.7 moles phosphorus per mole of framework aluminum, with a 0.5:1 ratio believed optimum.

Preferably the phosphorus compound is added to the FCC makeup catalyst at the catalyst plant using conventional techniques, typically adding some phosphoric acid to one of the catalyst forming solutions or spraying or impregnating the catalyst after forming and/or calcination. Phosphorus addition is beneficial in that it improves attrition resistance of the catalyst. Generally at least 1 wt % P (on a calcined catalyst basis) is needed to significantly improve attrition resistance. Phosphorus levels above about 3.5 wt %, finished catalyst basis, should be avoided because excessive P levels can cause crystal collapse on calcination.

The most preferred time to add phosphorus is to the faujasite, before mixing with amorphous matrix material. There is competition between alumina in the matrix and framework aluminum during phosphorus addition. By adding phosphorus to the neat zeolite it is possible to ensure that it will associate with the faujasite and stabilize it against collapse.

When the phosphorus is added after formation of the cracking catalyst or to E-Cat withdrawn from the FCC unit, much of the phosphorus ends up in less useful places than associated with framework alumina. Much more phosphorus is needed for this post-formation type of addition, and the phosphorus may not be as strongly held by zeolite.

Post FCC P conditioning usually starts with clean burned E-Cat from the regenerator. The phosphorus source may be any organic or inorganic phosphorus compound which is compatible with FCC E-Cat at these conditions. Suitable compounds include phosphoric acid, ammonium phosphates, hydrogen ammonium phosphates, trimethylphosphite, etc. The preferred compounds are phosphoric acid and ammonium hydrogen phosphates.

The phosphorus component may be added to the E-Cat after removal from the FCC unit, either in a separate catalyst impregnation stage, or by adding some phosphoric acid or other suitable phosphorus component to the base or an intermediate portion of the lift pipe 24, or to some portion of the hydrator 26. Phosphorus addition may be tailored to the incoming phosphorus content of the catalyst, i.e., add relatively large amounts of phosphorus if the E-Cat is essentially phosphorus free, and smaller amounts as phosphorus accumulates.

The E-Cat will usually contain many other additives, the most prevalent being an octane enhancing additive such as ZSM-5. Other additives which may be present include CO combustion promoter, DESOx additives, bottoms cracking additives, metals getters, etc. These additives are not especially preferred for alkylation but will be present because they were added at some time to the FCC unit, and remain for months in the FCC unit.

CATALYST HYDRATION

This is essential, as neither conventional E-Cat, E-cat from P stabilized faujasite, or phosphorus treated E-Cat has sufficient activity for use as an alkylation catalyst. Our hydration technique will, for a properly treated phosphorus containing faujasite catalyst, increase the activity, as measured by the alpha test, by at least 100%, and usually by 200%, preferably by 500% or more. The alpha test gives an alpha value, or alpha number, a measure of zeolite acidic functionality. This test is described in U.S. Pat. No. 4,016,218, J. Catalysis, 6, pp. 278–287 (1966) and J. Catalysis, 61, pp. 390–396 (1980). The conditions cited in the latter reference are used for characterizing the catalysts described herein.

The catalyst can be wet with water in a hydrator, but steam can hydrate the catalyst so long as the temperatures are not excessive. Thus use of wet steam, or low pressure steam as a lift medium in lift tube 24 can hydrate the catalyst.

Hydration should be long enough, and with enough water or steam present, to hydrate the catalyst and activate it, but not so long as to remove undue amounts of phosphorus nor introduce unnecessary water into the downstream alkylation reactor.

When P stabilization of neat faujasite, prior to catalyst formulation is practiced, the phosphorus is relatively stable and little will be lost to water washing. When post-catalyst formulation P-stabilization is practiced the phosphorus can be lost to a significant extent by water washing.

Water washing, and treatment with low pressure steam, will generally leave too much water associated with the catalyst for optimum results. Either the amount of steam and or water added can be carefully controlled to limit water addition, or the catalyst may be over-hydrated and dried or steamed to achieve the optimum water content.

The amount of water left on the catalyst after saturation with liquid water and heating to 350° C. is optimum for the alkylation reaction. Steaming at 350° C., or adding a controlled amount of water or steam, at a lower temperature to add the amount of water desired, may also be used.

ALKYLATION REACTOR FEED/OPERATING CONDITIONS

The alkylation reactor feed comprises isobutane and reactive light olefins. The feeds may be added separately or together. The alkylation catalyst may be added continuously or intermittently with one of the other feed streams.

The Garwood et al patent U.S. Pat. No. 3,251,902, which has been incorporated by reference, disclosed use of virgin REX catalyst for the same process. Thus this patent teaches temperatures, pressures, reaction conditions and feed compositions which will be generally suitable for the process of the present invention.

ALKYLATION UNIT PRODUCT RECOVERY

Conventional product recovery techniques may be used. In an extreme case, the alkylation reactor may rely entirely on the FCC reactor for product recovery. Thus the entire contents of the alkylation reactor may discharge into some portion of the FCC reactor circuit.

A slurry of catalyst and hydrocarbons, both liquid and vapor, may be mixed with the FCC feed, used as lift gas in the base of the riser, added to the top of the riser, preferably added to the stripper, or even discharged directly into the FCC main column. These approaches eliminate essentially all of the capital cost of product recovery (provided there is sufficient spare capacity in the FCC unit and/or fractionator) but still involve some penalty. There will be overcracking of alkylate if alkylate is used as lift gas. Adding alkylate + catalyst slurry to the main column will not overcrack alkylate but will add large amounts of solids to the FCC main column.

The availability of satisfactory "dumping grounds" for slurry products permits great economy in design of such V/L separators, fractionators etc as are installed for the alkylation section. Spare pumps and oversized fractionators are not needed, in an emergency all or part of any stream may be vented to some low pressure part of the FCC unit.

It usually will be preferred to recover two key streams, isobutane for recycle and alkylate. Each recovery stage is reviewed hereafter.

ISOBUTANE RECOVERY

Isobutane is a valuable resource in a refinery, and maximum use should be made of this in the alkylation reactor. A flash separator, or fractionator with a few trays or a modest depth of packing material can be used to recover a relatively concentrated iC4 fraction from the alkylation reactor effluent. This material may be sent to the unsaturated gas plant associated with the FCC, or compressed, condensed and recycled directly to the alkylation reactor. Conventional isobutane recovery technology, which is similar to that used in gas plants, may be used to recover and recycle isobutane.

ALKYLATE RECOVERY

Conventional product recovery techniques may be used. A rough cut fractionation or flashing between gasoline boiling range alkylate and heavier materials downstream of the alkylation reactor will be sufficient. Usually butane and lighter materials will have been flashed prior to alkylate recovery. The economics of the process are not greatly altered if some gasoline boiling range alkylate is charged to the cat cracker main column. This relaxed fractionation demand reduces the capital and operating expense of the alkylate flash unit.

EXAMPLE 1

Several REY based catalysts were prepared to evaluate their acid catalytic activities as a function of their pretreatment. In this example acid activity is gauged by hexane cracking at 1000° F. using the standard e test. For FCC catalyst applications, catalysts are normally formulated, spray dried, calcined (at about 1000° F., air, 17 hr) and steamed (1400° F., 100% steam, 5 hr). The steaming step generates a simulated equilibrium FCC catalyst. The catalysts of this study were tested with no modification and with phosphorus modification. Phosphorus modification consisted of impregnating a known amount of catalyst with sufficient phosphoric acid to provide the desired wt. % P in the final calcined solid. Impregnation was carried out by suspending the catalyst in an excess of water, adding the desired amount of 85% H₃PO₄, and evaporating off the water in a rotary evaporator. Hydration in this example was done by wetting the catalyst and then removing excess H₂O allowing the wetted catalyst to equilibrate with 100% humidity air at room temperature for 72 hrs. The activity results are summarized at the various stages of catalyst preparation below. In all of these examples, the REY catalyst was a 67% RE exchanged Y zeolite having an alumina content of 18%. The percent crystallinity, or %XTL was measured after steaming and was obtained by integrating the XRD intensity and comparing it to the XRD of the fresh REY catalyst.

|  |  | Catalyst Activity (α) |  |  |
|---|---|---|---|---|
| Catalyst | wt. % P | Calcined | Steamed | Rehydrated | % XTL |
| A) Fresh REY | 0.0 | 32 | 1 | 1 |  |
| B) Modified REY | 3.5 |  | 3 | 11.3 | 75 |
| C) Modified REY | 3.0 |  |  | 14 | 54 |
| D) Modified REY | 11 |  | <1 |  | 0 |

These results show that phosphorus modification of REY in the range of 3–4% P, provides an FCC catalyst with improved equilibrium activity and, after rehydration, is enhanced to substantial acid activity. With no P modification, rehydration does not respond in the same way. At high levels of P the crystallinity is lost on calcination and steaming and the catalyst is no more active than conventional amorphous materials.

EXAMPLE 2

The catalysts of example 1 were evaluated in isobutane/2-butene alkylation reactions conducted in a slurry reactor using the following procedure. Catalysts were crushed to <100 mesh then dried at 400° C. for 4 hrs in dry air. The catalyst was placed in a 300 cc stainless steel stirred autoclave and the reactor system was filled with isobutane. The slurry was stirred at 1900 rpm and heated to 70° C. A premixed feed of 1/50 mole ratio of 2-butene/isobutane containing 1% hexane (as an internal standard) was then added to the reactor such that the 2-butene feed rate was 0.1 WHSV. The reactor outlet was equipped with a 2μ filter so that the solid catalyst was retained in the reactor while the product was continuously withdrawn. After a sufficient time on stream, on line chromatographic analyses were conducted to evaluate the activity and selectivity of the catalysts. With the fresh calcined catalyst (1-A) good activity was noted for many hours and the quality of the product was very good, but when catalyst 1-A was steamed, little or no activity is noted and the quality is poor. Rehydration of this catalyst does not improve its performance. After 2.5 hrs on stream, the phosphorus treated catalyst (1-C), after steaming and rehydration, was observed to produce alkylate of high quality which had the following composition.

| Product | wt. % |
|---|---|
| Isopentane | 7.8 |
| 2,3-Dimethylbutane | 2.3 |
| 2,4-Dimethylpentane | 1.6 |
| 2,3-Dimethylpentane | 2.3 |
| 2,2,4-Trimethylpentane | 7.8 |
| 2,2,3-Trimethylpentane | 3.9 |
| 2,3,4-Trimethylpentane | 33.6 |
| 2,3,3-Trimethylpentane | 27.1 |
| 2,4-Dimethylhexane | 1.6 |
| 2,3-Dimethylhexane | 3.9 |
| 3,4-Dimethylhexane | 5.4 |
| C9⁺ paraffins | 3.9 |

EXAMPLE 3

The kinetic parameters for the catalysts of examples 1-A (calcined) and 1-C (steamed and rehydrated) were compared in a standard alkylation screening test in a fixed bed tubular reactor operating in single pass, liquid phase conditions which achieved a controlled partial conversion of the olefin feed. Initial conversions (during the first 1 minute of operation) were observed and are summarized below.

The catalysts were Grace REY ammonium exchanged, (i.e. Example 1-A above), pelleted (binder free), calcined, and crushed to 0.2 mm (60/80 mesh) and the P-treated version of this material indicated in example 1-C (also crushed to 60/80 mesh). Samples were charged with excess 80 mesh sand (e.g. 1–10 mg REY in ~400 mg sand). Packed density was 0.45 gm/cc; ash was 0.91. The REY catalysts were dried in situ at 350° C. to assure a uniform hydrated state. The alkylation feed consisted of an isopentane/2-butene mixture having an (I/O) feed ratio of 1200 g/g (930 molar). The space velocities reported are based on as received catalyst weight and either total feed volumetric rate (SV) or olefin mass feed weight (WHSV). Reaction conditions were 70° C. and 500 psig. Conversions were determined using n-heptane or 2,2 dimethyl butane as an internal standard. The liquid product was analyzed with a Varian gas chromatograph at maximum FID sensitivity using a 60 m DB-1.025 mm column.

The combined feed streams passed through a mixing section of ⅛" tubing (6 ml), a preheating zone of 1/16" tubing coiled around a brass rod, the reactor (a 10 cm section of ⅛ or ¼" tubing), and away from the reactor with 1/16" tubing through a −10° C. condenser and grove loader (internal space reduced with Teflon filler) to a sample bottle cooled with dry ice acetone. Total system volume was 9 ml. Reactor temperature was measured on the reaction tube wall and maintained in a 3 zone tube furnace. Feed streams were metered with ISCO syringe pumps. Catalyst was initially purged with nitrogen (GHSV>10*6) at 350° C. and atmospheric pressure for ~2 hours. The cooled reactor was then brought to 70° C. and 500 psi under isopentane flow at ~80% of the experimental SV [ml/hr g-cat]. Olefin feed was then introduced as a step input from a feed pump typically containing 0.2 to 0.4% t,2-butene in either n-pentane or isopentane carrier. The "initial" sample was collected between −2 and +2 minutes of the time the feed "step" reached the system exit.

The initial olefin conversion activities observed for the two REY catalysts are shown in the table below. Even at this high 2-butene dilution (I/O=1200) high isopentane alkylation activities were observed for both catalysts.

Effect of Catalyst Treatment on Initial Activity in Alkylation
(70° C. 500 psi Isopentane/2-Butene = 1200 g/g)

| Example | SV ml/g hr | WHSV (=) | % Butene Conv | % Butene Selectiv. to $C_9$ paraffins |
|---|---|---|---|---|
| 1A (REY) | 33600& | 13.2 | 19.3 | 0.61 |
| | 11000& | 4.3 | 66.9 | 0.74 |
| | 7700 | 3.9 | 68.2 | 0.64 |
| | 5600& | 2.2 | 89.7 | 0.73 |
| 1C (P-REY) | 2400 | 0.9 | 57.0 | 0.6** |

&indicates n-pentane present as 25% inert diluent
**average first 10 minutes of operation The major reaction product (~50–80% of butenes converted) was $C_9$ paraffins (mostly tri-methyl hexanes and dimethyl heptanes). The above Table presents the selectivity of butene conversion to $C_9$s. Traces of butane, and $C_8$ paraffins (less than NOTE that the phosphorus treated and stabilized material (Example 1-C) has very good activity as does the REY base case (Example 1-A). Further examination of the conversion activity of these catalysts shows olefin conversion is first order. The phosphorus stabilized severely steamed catalyst, Example 1-C, surprisingly retained about 20% of the activity of the unsteamed base case catalyst (Example 1-A).

We claim:

1. A combined fluidized catalyst cracking (FCC) and olefin alkylation process for conversion of 650° F.+ hydrocarbons to products including catalytically cracked naphtha and alkylate comprising:

contacting said feed with a stream of regenerated, phosphorus containing equilibrium faujasite cracking catalyst (E-Cat) having an average particle size within the range of 60–80 microns and an alpha activity in a cracking reactor to produce cracked products including naphtha boiling range material and light olefins including propylons and butylene and spent catalyst;

separating cracked products from spent catalyst in a product fractionator and gas purl ficat ion plant to produce a naphtha boiling range product and a light olefin product stream comprising at least one of propylene and butylene;

stripping spent catalyst with steam to produce stripped catalyst;

regenerating said stripped catalyst in a catalyst regeneration means by contact with an oxygen containing gas to produce regenerated, phosphorus containing E-Cat and flue gas containing entrained catalyst and fines;

recycling to said cracking reactor a major portion by weight of said regenerated E-Cat:

charging to an activation reactor a minor portion by weight of said regenerated E-Cat and activating said E-Cat by contact with water or steam at catalyst activation conditions sufficient to increase the alpha activity of the E-Cat at least 100% and produce activated E-Cat;

charging said activated E-Cat to an alkylation reactor for use as alkylation catalyst;

alkylating at olefin alkylation conditions in said alkylation reactor isobutane and at least a portion of said light olefinic product comprising at least one of propylene and butylene to produce alkylate and spent alkylation catalyst;

recovering by settling, flashing, or fractionation alkylate from spent alkylation catalyst to produce alkylate as a product of said alkylation process and to produce spent alkylation catalyst;

recycling, at least periodically, said spent alkylation catalyst to said regenerator.

2. The process of claim 1 wherein catalyst is activated by contact with at least one member of the group of liquid water, steam, and mixtures thereof, to form an overhydrated alkylation catalyst which is then dried or dehydrated to produce a hydrated alkylation catalyst having an alpha activity increased by at least 100%.

3. The process of claim 1 wherein said slurry is mixed with isobutane and added to a continuous stirred tank reactor (CSTR) wherein said light olefin product is added.

4. The process of claim 1 wherein a slurry of catalyst and unreacted isobutane is continuously withdrawn from said CSTR and isobutane recovered therefrom by flashing.

5. The process of claim 1 wherein the faujasite is zeolite X.

6. The process of claim 1 wherein the faujasite is zeolite Y.

7. The process of claim 1 wherein the equilibrium catalyst contains from 10 to 40 wt % faujasite, based on the zeolite content of makeup catalyst to the FCC unit.

8. The process of claim 1 wherein activation increases the alpha activity at least 200%.

9. The process of claim 1 wherein the amount of phosphorus present relative to aluminum in faujasite structure ranges from 0.1:1 to 1:1, molar basis.

10. The process of claim 7 wherein the amount of phosphorus present relative to aluminum in faujasite structure ranges from 0.3:1 to 0.7:1, molar basis.

* * * * *